US00PP15967P3

(12) United States Plant Patent
Preil et al.

(10) Patent No.: US PP15,967 P3
(45) Date of Patent: Sep. 20, 2005

(54) ***RHODODENDRON* ROOTSTOCK NAMED 'RHODUNTER 48'**

(50) Latin Name: ***Rhododendron* hybrid**
Varietal Denomination: Rhodunter 48

(75) Inventors: Walter Preil, Ammersbek (DE); Rainer Ebbinghaus, Ahrensburg (DE)

(73) Assignee: Inkarho GmbH, Bad Zwischenahn (DE)

( * ) Notice: Subject to any disclaimer, the term of this patent is extended or adjusted under 35 U.S.C. 154(b) by 0 days.

(21) Appl. No.: 10/270,093

(22) Filed: Oct. 11, 2002

(65) Prior Publication Data

US 2004/0073980 P1 Apr. 15, 2004

(51) Int. Cl.[7] ..... A01H 5/00
(52) U.S. Cl. ..... Plt./238
(58) Field of Search ..... Plt./238

*Primary Examiner*—Kent Bell
(74) *Attorney, Agent, or Firm*—Webb Ziesenheim Logsdon Orkin & Hanson, P.C.

(57) ABSTRACT

A new and distinct *Rhododendron* hybrid plant used as a rootstock or flowering shrub that exhibits hardy and vigorous growth.

2 Drawing Sheets

Botanical classification: *Rhododendron* hybrid.
Varietal denomination: 'Rhodunter 48'.

BACKGROUND OF THE INVENTION

The present invention comprises a new and distinct cultivar of *Rhododendron* hybrid used as a flowering shrub or rootstock known by the varietal name 'Rhodunter 48'. The new variety was discovered in Ahrensburg, Germany. The new variety is the result of a planned breeding program between an unpatented and unnamed plant of *Rhododendron fortunei* (female parent)×cv. 'Cunningham's White' (unpatented male parent). The new variety exhibits matroclinal morphological features. 'Rhodunter 48' exhibits distinct but similar leaf venation to both parents, as well as similarities in color and shape. The new variety has been trial and field tested and has been found to retain its distinctive characteristics and remain true to type through successive propagations.

DESCRIPTION OF THE DRAWINGS

The accompanying photographic drawings illustrate the new cultivar, with the color being as nearly true as is possible with color illustrations of this type.

DESCRIPTION OF THE PLANT

Figure 1:
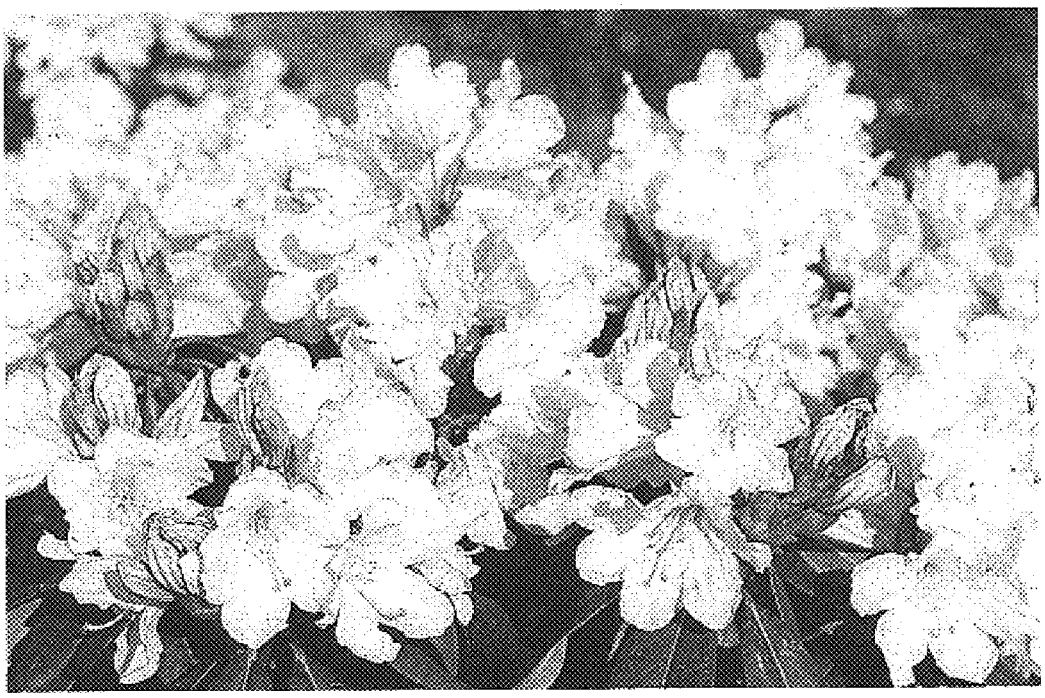
FIG. 1 shows a close-up view of the flowers of the new variety.
Figure 2:
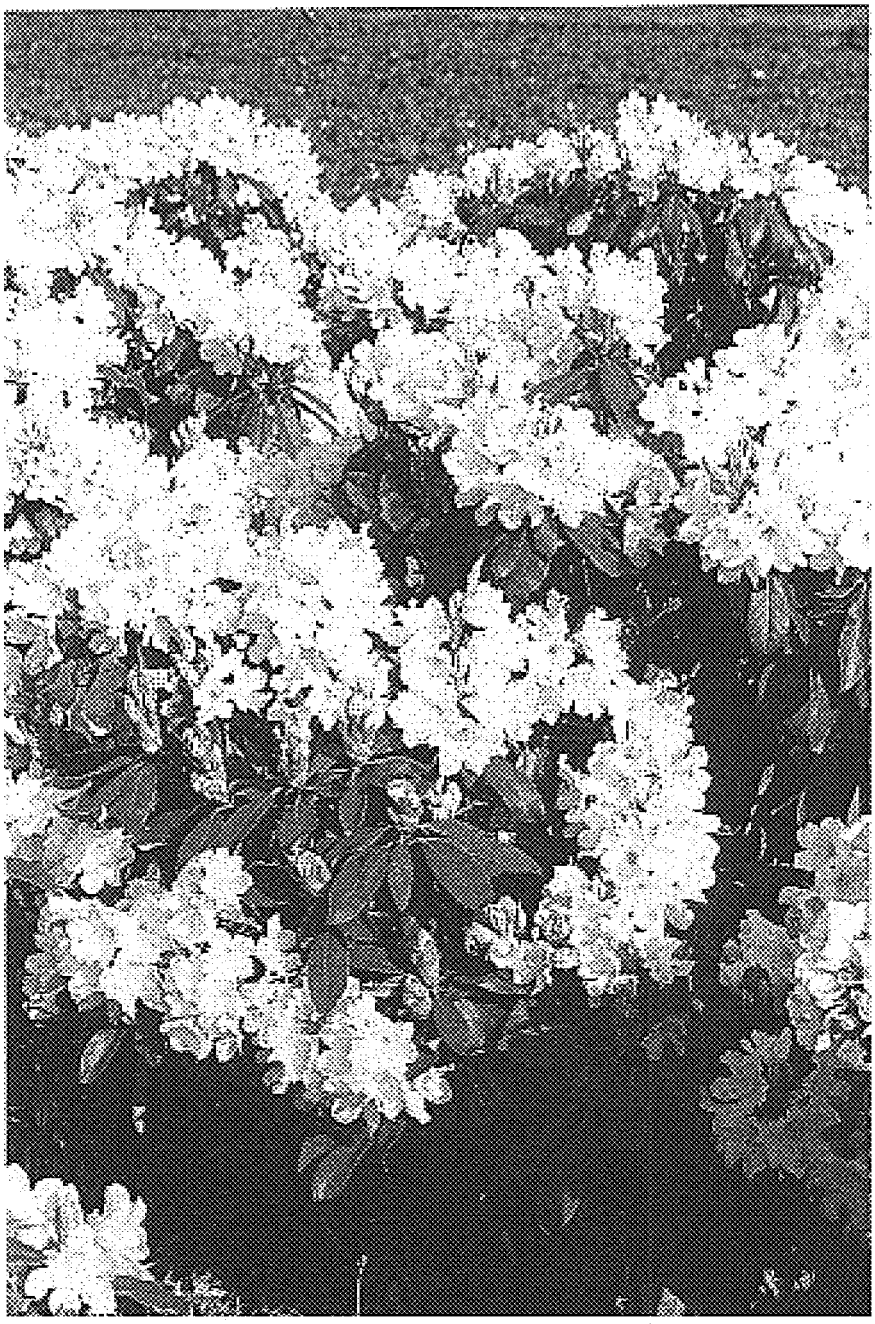
FIG. 2 shows the new variety grown to a flowering plant.

The following detailed description sets forth the characteristics of the new cultivar. The data which defines these characteristics were collected by asexual reproductions performed using tissue culture medium for shoot multiplication of *Rhododendron* species and which were carried out in Ahrensburg, Germany. The color readings were taken in natural daylight. The field-grown plants were five years old when described (unless indicated otherwise). The soil was a sandy loam mixed with peat. Color references are primarily to The R.H.S. Colour Chart of The Royal Horticultural Society of London.

PLANT

Type: Evergreen shrub.
Use: Flowering shrub or rootstock.
Soil: Sandy loam.
Light: Full.
Fruit bearing: Very low.
Crop time: 1.5 years is required to achieve finished product size that is ready for use as a rootstock or 4 years for use as a flowering shrub.
Dimensions at crop time (3 years after grafting. Dimensions depend on the vigor of the scion cultivar):
- *Height.*—50 cm.
- *Width.*—40 cm.

Vigor: 120% of standard using 'Nova Zembla' (unpatented) as the standard.
Habit: Erect.
Hardiness: USDA zone 6a.
Rooting habit: Compact root bales.
Time to initiate roots: 3 months at 22–25° C. for softwood cuttings.
Disease and pest resistance: No observation made to date.
Trunk (at 4 years):
- *Diameter.*—3 cm.
- *Height.*—5 cm above soil.
- *Bark color.*—Surface: Year 1: 147A. Year 2: 144A to 175A. Year 3: 175A. Year 4: 177B to 197B to 197C. Flesh: 157B.
- *Lenticels.*—Inconspicous.

Branches:
- *Color.*—Surface: Year 1: 147A. Year 2: 144A to 175A. Year 3: 175A. Year 4: 177B to 197B to 197C. Flesh: 157B.
- *Length* (*at one year*).—22 cm.
- *Base diameter* (*at one year*).—9 mm.
- *Texture.*—Hard.
- *Internode length.*—1–2 cm.
- *Branching angle at emergence.*—45° angle.
- *Habit.*—Compact.
- *Pubescence.*—Absent.
- *Branch lenticels.*—Inconspicous.

Leaves:
- *Arrangement.*—Alternate.
- *Length.*—20 cm maximum.

*Width.*—7.5 cm maximum.
*Shape.*—Oblanceolate.
*Apex.*—Truncated.
*Base.*—Triangular.
*Color.*—Adaxial: 147A. Abaxial: 147C.
*Surface.*—Adaxial: Glabrous. Abaxial: Glabrous.
*Margins.*—Entire.
*Division.*—Undivided.
*Petiole.*—Length: 2 cm. Width: 3–4 mm. Color: Between 144A and 166B. Surface: Glabrous.
*Leaf stipules.*—Sessile.
*Leaf pubescence.*—Absent.
*Venation pattern.*—Feather-veined.
*Vein color.*—Adaxial: 144A. Abaxial: 145C.
*Leaf texture.*—Hard.
*Leaf appearance.*—Typical *Rhododendron* leaf.

Fruit: Fruits (capsules) are usually absent due to self-sterility or incompability with other *Rhododendrons*. When present, the seed color is 164B.

Flower:
*Arrangement.*—Single.
*Shape.*—Widely funnel-shaped.
*Bud.*—Shape: Oblong; Ellipsoid. Width: 20 mm. Length: 40 mm. Color: Closed: 186B. Before bursting: 65B. Time of bloom: At 2 years old. Lastingness of bloom: 21 days.
*Diameter.*—8 cm.
*Depth.*—20 mm.
*Bloom quantity.*—11–15 per truss.

Petal:
*Shape.*—Fused; the corolla has a wide funnel shape.
*Number.*—7.
*Length.*—45–55 mm.
*Width of corolla.*—70–80 mm.
*Apex.*—Round.
*Margin.*—Undulate.
*Color* (*when fully open*).—Upper surface: 158B. Lower surface: 159C.
*Peduncle.*—Length: 4 cm. Width: 2 mm. Surface: Glabrous. Color: Upper surface: 179B. Lower surface: 144C.

Sepals: Not present.
Petaloids: Not present.
Natural flowering season: Beginning of May through the end of May.
Fragrance: *Rhododendron* fortunei-like.

REPRODUCTIVE ORGANS

Stamens:
*Number.*—14.
*Length.*—30 mm.
*Color.*—150D.

Anthers:
*Shape.*—Normal *Rhododendron* type.
*Color.*—161D.
*Length.*—25 mm.
*Width.*—1 mm.
*Amount of pollen.*—Medium.
*Color of pollen.*—150D.
*Stigma color.*—145A.

Pistil:
*Length.*—5 cm.
*Number.*—1.

Style:
*Color.*—150C.
*Form.*—Filiform.
*Length.*—45 mm.
*Width.*—1 mm.

Ovaries:
*Length.*—5 mm.
*Width.*—3 mm.
*Color.*—137C.
*Position.*—Superior.

I claim:

1. A new and distinct variety of *Rhododendron* hybrid plant as illustrated and described.

* * * * *